United States Patent [19]

Cantatore et al.

[11] Patent Number: 4,992,493
[45] Date of Patent: Feb. 12, 1991

[54] PIPERIDINE-TRIAZINE COMPOUNDS FOR USE AS STABILIZERS FOR ORGANIC MATERIALS

[75] Inventors: Giuseppe Cantatore, Bitonto; Valerio Borzatta, Bologna; Franca Masina, Anzola Emilia, all of Italy

[73] Assignee: Ciba-Geigy Corporation, Ardsley, N.Y.

[21] Appl. No.: 403,559

[22] Filed: Sep. 6, 1989

Related U.S. Application Data

[62] Division of Ser. No. 217,962, Jul. 11, 1988, Pat. No. 4,883,870.

[30] Foreign Application Priority Data

Jul. 16, 1987 [IT] Italy .................. 21320 A/87

[51] Int. Cl.$^5$ .......................................... C08K 5/3435
[52] U.S. Cl. .................................... 524/97; 524/98; 524/100; 252/401; 252/403
[58] Field of Search ............... 252/401; 524/403, 97, 524/98, 100

[56] References Cited

U.S. PATENT DOCUMENTS

| | | | |
|---|---|---|---|
| 4,108,829 | 8/1978 | Cassandrini et al. | 524/101 |
| 4,731,393 | 3/1988 | Karrer et al. | 522/117 |
| 4,769,443 | 9/1988 | Cantatore | 528/423 |
| 4,785,102 | 11/1988 | Berner et al. | 546/20 |
| 4,816,507 | 3/1989 | Cantatore et al. | 524/100 |
| 4,843,159 | 6/1979 | Cantatore et al. | 544/113 |
| 4,863,981 | 9/1989 | Gugumus | 524/100 |
| 4,883,870 | 11/1989 | Cantatore et al. | 524/100 |

FOREIGN PATENT DOCUMENTS 0117229  8/1984  European Pat. Off. .

*Primary Examiner*—Kriellion Morgan
*Attorney, Agent, or Firm*—JoAnn Villamizar

[57] ABSTRACT

The compounds of the formula (I)

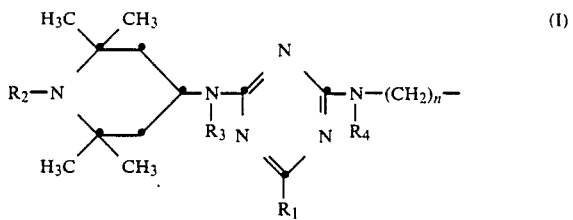

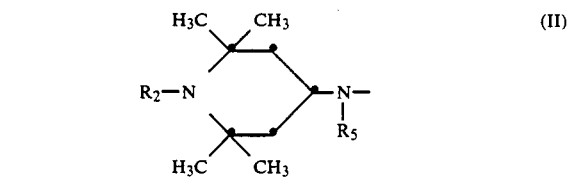

in which
$R_1$ is $C_1$–$C_8$-alkyloxy, allyloxy, allylamino, di($C_1$–$C_4$-alkyl)-amino, diallylamino, a 5-membered to 7-membered nitrogen containing heterocyclic group with the nitrogen atom linked to the triazine ring, or a group of the formula (II),

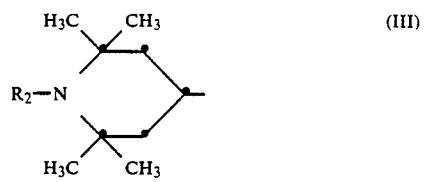

$R_2$ is hydrogen, O, OH, NO, $CH_2CN$, $C_1$–$C_8$-alkyl, allyl, benzyl, $C_1$–$C_8$-acyl, $C_1$–$C_{18}$-alkyloxy, $C_5$–$C_{12}$-cycloalkyloxy or OH-monosubstituted $C_2$–$C_4$-alkyl, $R_3$ and $R_5$ independently are hydrogen, $C_1$–$C_{12}$-alkyl, $C_5$–$C_{12}$-cycloalkyl, $C_7$–$C_9$-phenylalkyl, tetrahydrofurfuryl, $C_2$–$C_4$-alkyl monosubstituted by OH, by $C_1$–$C_4$-alkyloxy or by di($C_1$–$C_4$-alkyl)amino, or a group of the formula (III)

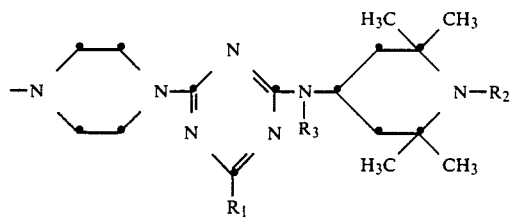

with $R_2$ as defined above, $R_4$ is hydrogen, $C_1$–$C_{12}$-alkyl or cyclohexyl and n is an integer from 2 to 6, are useful as light stabilizers, heat stabilizers and oxidation stabilizers for organic materials, in particular synthetic polymers.

6 Claims, No Drawings

PIPERIDINE-TRIAZINE COMPOUNDS FOR USE AS STABILIZERS FOR ORGANIC MATERIALS

This is a divisional of U.S. patent application Ser. No. 217,262 filed on July 11, 1988 now U.S. Pat. No. 4,883,870.

The present invention relates to novel piperidine-triazine compounds, the use thereof as light stabilizers, heat stabilizers and oxidation stabilizers as well as to the stabilized organic materials, especially synthetic polymers.

It is known that synthetic polymers undergo progressive changes of the physical properties, such as loss of mechanical strength and colour change, when they are subjected to the action of sunlight or other sources of ultraviolet light in the presence of oxygen.

To retard the photo-oxidative degradation of synthetic polymers it has been proposed to use diverse additives having light-stabilizing properties, such as certain derivatives of benzophenone and benzotriazole, nickel complexes, substituted benzoic acid esters, alkylidene-malonates, cyano-acrylates, aromatic oxamides and sterically hindered amines.

Certain triazine derivatives of 2,2,6,6-tetramethylpiperidine and their use as stabilizers for synthetic polymers are disclosed in US-A-4,108,829 and EP-A-117,229.

The present invention relates to novel piperidine-triazine compounds of the formula (I)

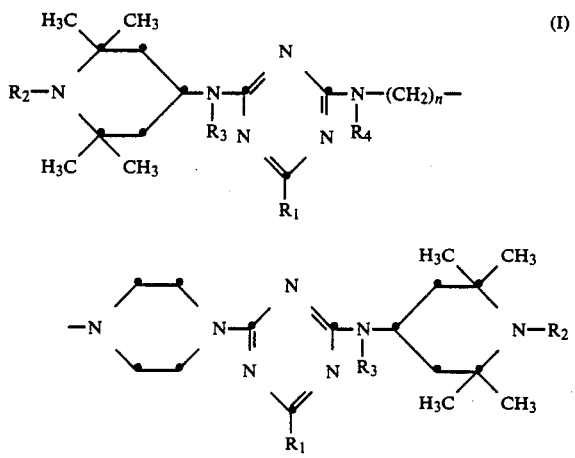

in which
$R_1$ is $C_1-C_8$alkyloxy, allyloxy, allylamino, di($C_1-C_4$-alkyl)amino, diallylamino, a 5-membered to 7-membered nitrogen containing heterocyclic group with the nitrogen atom linked to the triazine ring, or a group of the formula (II),

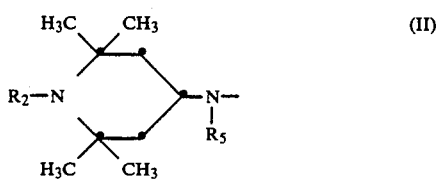

$R_2$ is hydrogen, $O^\cdot$, OH, NO, $CH_2CN$, $C_1-C_8$alkyl, allyl, benzyl, $C_1-C_8$acyl, $C_1-C_{18}$-alkyloxy, $C_5-C_{12}$-cycloalkyloxy or OH-monosubstituted $C_2-C_4$-alkyl, $R_3$ and $R_5$ independently are hydrogen, $C_1-C_{12}$-alkyl, $C_5-C_{12}$-cycloalkyl, $C_7-C_9$phenylalkyl, tetrahydrofurfuryl, $C_2-C_4$-alkyl monosubstituted by OH, by $C_1-C_4$-alkyloxy or by di($C_1-C_4$-alkyl)amino, or a group of the formula (III)

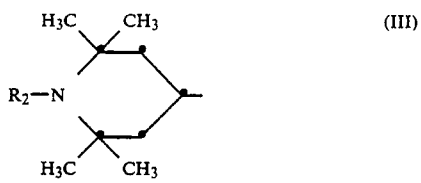

with $R_2$ as defined above, $R_4$ is hydrogen, $C_1-C_{12}$-alkyl or cyclohexyl and n is an integer from 2 to 6.

Representative examples of $R_1$ as $C_1-C_8$alkyloxy are methoxy, ethoxy, propoxy, isopropoxy, butoxy, isobutoxy, t-butoxy, hexyloxy and octyloxy. $C_1-C_4$-alkyloxy is preferred.

Representative examples of $R_1$ as di($C_1-C_4$-alkyl)amino are dimethylamino, diethylamino, dipropylamino, diisopropylamino, dibutylamino and diisobutylamino. Dimethylamino and diethylamino are preferred.

Representative examples of $R_1$ as a 5-membered to 7-membered nitrogen containing heterocyclic group are 1-pyrrolidyl, 1-piperidyl, 4-morpholinyl, 1-hexahydroazepinyl and 4-methyl-1-piperazinyl. 4-Morpholinyl is preferred.

Representative examples of $R_2$ as $C_1-C_8$alkyl are methyl, ethyl, propyl, butyl, pentyl, hexyl, heptyl and octyl. $C_1-C_4$-alkyl, in particular methyl, is preferred.

$R_2$ as $C_1-C_8$acyl may be an aliphatic or aromatic acyl group. Examples are formyl, acetyl, propionyl, butyryl, valeryl, hexanoyl, octanoyl, benzoyl, acryloyl and crotonoyl. $C_1-C_8$alkanoyl, $C_3-C_8$-alkenoyl and benzoyl are preferred. Acetyl is especially preferred.

Representative examples of $R_2$, $R_3$ and $R_5$ as $C_2-C_4$-alkyl monosubstituted by OH, preferably in the 2, 3 or 4 position, are 2-hydroxyethyl, 2-hydroxypropyl, 3-hydroxypropyl, 2-hydroxybutyl and 4-hydroxybutyl. 2-Hydroxyethyl is especially preferred.

$R_2$ as $C_1-C_{18}$-alkyloxy is for example methoxy, ethoxy, n-propoxy, n-butoxy, sec-butoxy, tert-butoxy, n-hexyloxy, n-octyloxy, 2-ethylhexyloxy, n-nonyloxy, n-decyloxy, n-undecyloxy, n-dodecyloxy, n-tridecyloxy, n-tetradecyloxy, n-hexadecyloxy or n-octadecyloxy. $C_6-C_{12}$-alkyloxy, in particular heptyloxy and octyloxy, is preferred.

$R_2$ as $C_5-C_{12}$-cycloalkyloxy is for example cyclopentyloxy, cyclohexyloxy, cyclooctyloxy, cyclononyloxy or cyclododecyloxy. Cyclopentyloxy and cyclohexyloxy are preferred.

Representative examples of $R_3$, $R_4$ and $R_5$ as $C_1-C_{12}$-alkyl are methyl, ethyl, propyl, isopropyl, butyl, 2-butyl, isobutyl, t-butyl, pentyl, hexyl, heptyl, octyl, 2-octyl, 2-ethylhexyl, nonyl, decyl and dodecyl. $R_3$ and $R_5$ as $C_1-C_8$alkyl are preferred.

Examples of $R_3$ and $R_5$ as $C_5-C_{12}$-cycloalkyl are cyclopentyl, cyclohexyl, methylcyclohexyl, dimethylcyclohexyl, trimethylcyclohexyl, cyclooctyl and cyclododecyl. A cycloalkyl group of the formula —CH(CH$_2$)$_a$ with a being an integer from 4 to 7 is preferred. Said group may optionally be substituted by $C_1-C_4$-alkyl, in particular methyl. Cyclohexyl is especially preferred.

Representative examples of $R_3$ and $R_5$ as $C_7$-$C_9$-phenylalkyl are benzyl, methylbenzyl, dimethylbenzyl and 2-phenylethyl. Benzyl unsubstituted or substituted at the phenyl ring by one or two methyl groups is preferred.

Representative examples of $R_3$ and $R_5$ as $C_2$-$C_4$-alkyl monosubstituted by $C_1$-$C_4$-alkyloxy, preferably in the 2, 3 or 4 position, are 2-methoxyethyl, 2-ethoxyethyl, 2-butoxyethyl, 3-methoxypropyl, 3-ethoxypropyl, 3-butoxypropyl and 4-methoxybutyl.

Representative examples of $R_3$ and $R_5$ as $C_2$-$C_4$-alkyl monosubstituted by di($C_1$-$C_4$-alkyl)amino, preferably in the 2, 3 or 4 position, are 2-dimethylaminoethyl, 2-diethylaminoethyl, 2-dibutylaminoethyl, 3-dimethylaminopropyl, 3-diethylaminopropyl, 3-dipropylaminopropyl and 3-dibutylaminopropyl.

Those compounds of the formula (I) are preferred, in which $R_1$ is $C_1$-$C_4$-alkyloxy, allyloxy, allylamino, di($C_1$-$C_3$-alkyl)amino, diallylamino, 1-pyrrolidyl, 1-piperidyl, 4-morpholinyl, 1-hexahydroazepinyl or a group of the formula (II), $R_2$ is hydrogen, $CH_2CN$, $C_1$-$C_4$-alkyl, allyl, benzyl, acetyl or OH-monosubstituted $C_2$-$C_3$-alkyl, $R_3$ and $R_5$ independently are hydrogen, $C_1$-$C_{12}$-alkyl, cyclohexyl, benzyl, tetrahydrofurfuryl, $C_2$-$C_3$-alkyl monosubstituted by OH, by $C_1$-$C_4$-alkyloxy or by di($C_1$-$C_3$-alkyl)amino, or a group of the formula (III), $R_4$ is hydrogen, $C_1$-$C_4$-alkyl or cyclohexyl and n is 2 or 3.

Those compounds of the formula (I) are particularly preferred, in which $R_1$ is $C_1$-$C_3$-alkyloxy, allyloxy, allylamino, dimethylamino or diethylamino, diallylamino, 4-morpholinyl or a group of the formula (II), $R_2$ is hydrogen, methyl, allyl, benzyl, acetyl or 2-hydroxyethyl, $R_3$ and $R_5$ independently are hydrogen, $C_1$-$C_8$alkyl, cyclohexyl, benzyl, tetrahydrofurfuryl, $C_2$-$C_3$-alkyl monosubstituted by OH, by methoxy, by ethoxy, by dimethylamino or by diethylamino, or a group of the formula (III), $R_4$ is hydrogen or $C_1$-$C_3$alkyl and n is 2 or 3.

Those compounds of the formula (I) are of special interest, in which $R_1$ is 4-morpholinyl or a group of the formula (II), $R_2$ is hydrogen or methyl, $R_3$ and $R_5$ independently are $C_1$-$C_8$alkyl, tetrahydrofurfuryl, 2,2,6,6-tetramethyl-4-piperidyl or 1,2,2,6,6-pentamethyl-4-piperidyl, $R_4$ is hydrogen or methyl and n is 2.

Those compounds of the formula (I) are of particular interest, in which $R_1$ is a group of the formula (II), $R_2$ is hydrogen or methyl, $R_3$ and $R_5$ independently are $C_1$-$C_4$-alkyl, 2,2,6,6-tetramethyl-4-piperidyl or 1,2,2,6,6-pentamethyl-4-piperidyl, $R_4$ is hydrogen or methyl and n is 2.

$R_2$ is preferably hydrogen or methyl.

Preferred examples of compounds of the formula (I) are: 1-[2-[[2,4-bis[N-(2,2,6,6-tetramethyl-4-piperidyl)ethylamino]-1,3,5-triazin-6-yl]amino]ethyl]-4-[2,4-bis[N-(2,2,6,6-tetramethyl-4-piperidyl)-ethylamino]-1,3,5-triazin-6-yl]piperazine, 1-[2-[[2,4-bis[N-(2,2,6,6-tetramethyl-4-piperidyl)-n-butylamino]-1,3,5-triazin-6-yl]amino]ethyl]-4-[2,4-bis[N-(2,2,6,6-tetramethyl-4-piperidyl)-n-butylamino]-1,3,5-triazin-6-yl]piperazine, 1-[2-[[2,4-bis[N,N-bis(2,2,6,6-tetramethyl-4-piperidyl)amino]-1,3,5-triazin-6-yl]amino]ethyl]-4-[2,4-bis[N,N-bis(2,2,6,6-tetramethyl-4-piperidyl)amino]-1,3,5-triazin-6-yl]piperazine, 1-[2-[[2,4-bis[N-(1,2,2,6,6-pentamethyl-4-piperidyl)ethylamino]-1,3,5-triazin-6-yl]amino]ethyl]-4-2,4-bis[N-(1,2,2,6,6-pentamethyl-4-piperidyl)ethylamino]-1,3,5-triazin-6-yl]piperazine, or 1-[2-[[2,4-bis]N-(1,2,2,6,6-pentamethyl-4-piperidyl)-n-butylamino]-1,3,5-triazin-6-yl]amino]ethyl]-4-[2,4-bis[N-(1,2,2,6,6-pentamethyl-4-piperidyl)n-butylamino]-1,3,5-triazin-6-yl]piperazine.

The compounds of the formula (I) can be prepared by processes known per se, for example by reacting, in any desired order, cyanuric chloride with compounds of the formula (IV), (V) and (VI)

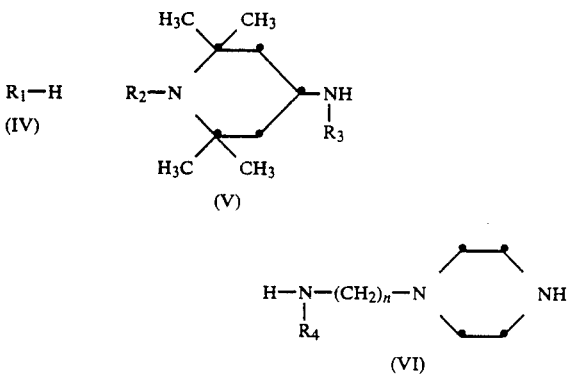

in which $R_1$, $R_2$, $R_3$, $R_4$ and n are as defined above.

The reactions are conveniently carried out in organic solvents such as e.g. t-butanol, t-pentanol, acetone, methyl ethyl ketone, methyl isobutyl ketone, dioxane, tetrahydrofuran, dibutyl ether, benzene, toluene, xylene, trimethylbenzene, ethylbenzene, decalin, octane, decane, chlorobenzene or N-methylpyrrolidone, in the presence of an organic or inorganic base, preferably sodium or potassium hydroxide or carbonate, in a quantity at least equivalent to the hydrochloric acid liberated in the reaction.

The substitution of the first chlorine of the cyanuric chloride is preferably carried out at temperatures between $-30°$ and $40°$ C., in particular between $-10°$ and $30°$ C., the substitution of the second chlorine is preferably carried out between $40°$ and $120°$ C., in particular between $50°$ and $100°$ C., and the substitution of the third chlorine is preferably carried out between $100°$ and $200°$ C., in particular between $120°$ and $180°$ C.

The various stages of the reactions can be carried out in a single reactor and in the same reaction medium without isolating the intermediates, or after the latter have been separated off and, if desired, purified.

As indicated at the outset, the compounds of the formula (I) are very effective in improving the light stability, heat stability and oxidation stability of organic materials, in particular synthetic polymers and copolymers. Especially, the outstanding oxidation stabilizing efficiency of the instant compounds is surprising.

Therefore, a further object of the invention is a composition comprising an organic material subject to thermal, oxidative or light-induced degradation and at least one compound of the formula (I).

Examples of organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/ acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in (1) above, for example polypropylene/ethylene-propylene-copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/ styrene, styrene/ isoprene/ styrene, styrene/ethylene/butylene/ styrene or styrene/ ethylene/ propylene/styrene.

6. Graft copolymers of styrene or a-methylstyrene such as, for example, styrene on polybutadiene, styrene on polybutadiene-styrene or poly-butadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9 Copolymers from the monomers mentioned under 8) with each other or with other unsaturated monomers, such as, for instance, acrylonitrile/ butadiene, acrylonitrile/alkyl acrylate, acrylonitrile/alkoxyalkyl acrylate or acrylonitrile/vinyl halogenide copolymers or acrylonitrile/ alkyl methacrylate/-butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-bis(4-hydroxyphenyl)propane] terephthalate and polyhydroxybenzoates as well as block-copolyether-esters derived from polyethers having hydroxyl end groups.

18. Polycarbonates and polyester-carbonates.
19. Polysulfones, polyether-sulfones and polyether-ketones.
20. Crosslinked polymers which are derived from aldehydes on the one hand and phenols, ureas and melamines on the other hand, such as phenol/formaldehyde resins, urea/formaldehyde resins and melamine/ formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.
23. Thermosetting acrylic resins, derived from substituted acrylic esters, such as epoxy-acrylates, urethane-acrylates or polyesteracrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.
27. Mixtures of polymers as mentioned above, for example Pp/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/ thermoplastic PUR, POM/acrylate, POM/MBS, PPE/HIPS, PPE/PA 6.6 and copolymers, PA/HDPE, PA/PP, PA/PPE.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.
29. Aqueous emulsions of natural or synthetic rubber, e.g. natural latex or latices of carboxylated styrene/butadiene copolymers. The compounds of the formula (I) are particularly suitable for improving the light stability, heat stability and oxidation stability of polyolefins, especially polyethylene and polypropylene.

The compounds of the formula (I) can be mixed with the material to be stabilized in various proportions depending on the nature of the polymer, the end use and the presence of other additives.

In general, it is appropriate to use 0.01 to 5 % by weight of the compounds of the formula (I), relative to the weight of the polymers, preferably from 0.05 to 1 %. The compounds of the formula (I) can be incorporated into the polymeric materials by various processes, such as dry blending in the form of powders, or wet mixing in the form of solutions or suspensions or also in the form of a masterbatch; in these operations, the polymer can be employed in the form of powder, granules, solutions, suspensions or in the form of a latex.

The polymers stabilized with the products of the formula (I) can be used for the preparation of moulded articles, films, tapes, monofilaments, surface-coatings and the like.

If desired, other additives, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the synthetic polymers.

Examples of additives which can be mixed with the compounds of the formula (I) are in particular:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(o-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1 2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tertbutyl-4-methylphenol), 2,2'-thiobis(4-octylphenol), 4,4'-thiobis(6-tertbutyl-3-methylphenol), 4,4'-thiobis(6-tert-butyl-2-methylphenol).

1.4. Alkylidenebisphenols, for example 2,2'-methylenebis(6-tert-butyl4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis-[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tertbutyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6 Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl) oxalic acid diamide.

1.10. Amides of B-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)-hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-secbutyl-5'-tert-butyl, 4'-octoxy, 3',5'-di-tert-amyl and 3',5'-bis-(α,αdimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4,-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β, β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-(2-hydroxyethyl)-2,2,6,6-tetramethyl-b 4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)bis-(3,3,5,5-tetramethylpiperazinone).

2.7. Oxalic acid diamides, for example 4,4'-dioctyloxyoxanilide, 2,2'dioctyloxy-5,5'-di-tert-butyloxanilide, 2,2'-didodecyloxy-5,5'-di-tertbutyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o-and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide 4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Na ricinoleate and K palmitate, antimony pyroholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The following examples illustrate the present invention:

EXAMPLE 1:

68.12 g (0.4 mol) of N-(2,2,6,6-tetramethyl-4-piperidyl)-methylamine are added slowly to a solution of 36.88 g (0.2 mol) of cyanuric chloride in 300 ml of xylene cooled to 10° C., while maintaining the temperature between 10° and 15° C.

After the end of the addition, the mixture is stirred for 1 hour at ambient temperature, and the solution of 16.8 g (0.42 mol) of sodium hydroxide in 70 ml of water is then added.

The mixture is heated for 2 hours at 60° C. and the added water separated off and 12.92 g (0.1 mol) of N-2-aminoethylpiperazine and 12 g (0.3 mol) of sodium hydroxide are then added. The mixture is heated for 3 hours under total reflux and then for a further 16 hours while separating off the water of reaction.

The mixture is filtered and evaporated in vacuo (26 mbar), and the residue is crystallized from hexane.

After drying, the product of the formula

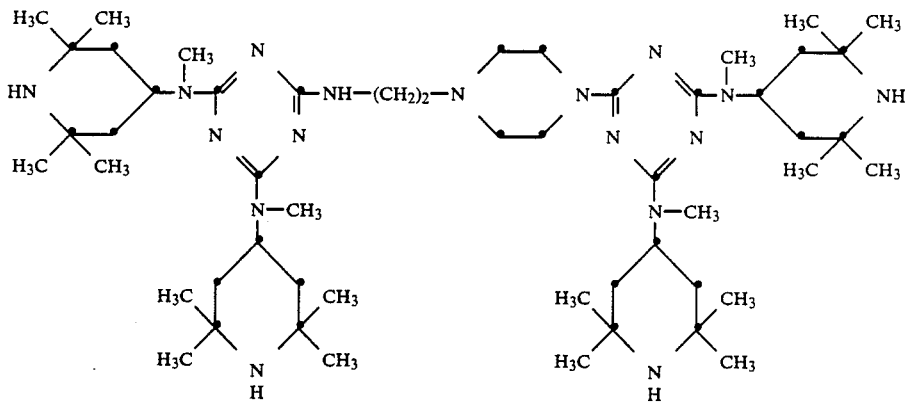

of melting point=171°–174° C. is obtained.

Analysis for $C_{52}H_{97}N_{17}$:
Calculated C=65.03%, H=10.18%, N=24.79%
Found: C=64.82%, H=10.12%, N=24.84%

EXAMPLES 2-5:

Proceeding analogously to Example 1 and using the appropriate reagents, the following compounds of the formula

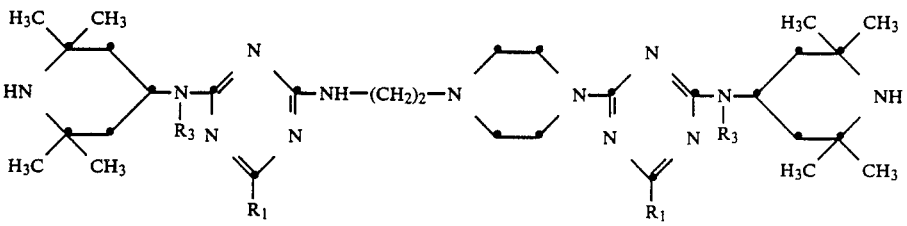

are obtained.

| Example | $R_1$ | $R_3$ | Melting point (°C.) |
|---|---|---|---|
| 2 | ![piperidyl with N-C2H5] | $-C_2H_5$ | 229–230 |
| 3 | ![piperidyl with N-C4H9-n] | $-C_4H_9\text{-}n$ | 184–186 |
| 4 | ![bis-piperidyl group, subscript 2] | ![tetramethylpiperidyl NH] | 300–305 |

-continued

| Example | R₁ | R₃ | Melting point (°C.) |
|---|---|---|---|
| 5 | —NH—CH₂—CH=CH₂ | (2,2,6,6-tetramethylpiperidin-4-yl-NH) | 223-224 |

EXAMPLE 6:

81.3 g (0.08 mol) of the compound of Example 2 are dissolved at ambient temperature in a solution of 20.71 g (0.45 mol) of formic acid in 80 ml of water.

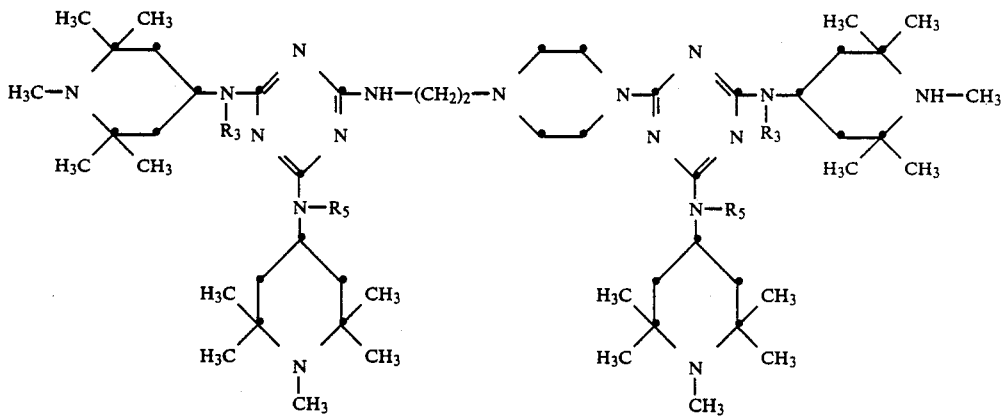

10.8 g (b 0.36 mol) of paraformaldehyde are added to the solution obtained, and the mixture is heated for 10 hours under reflux.

After cooling to ambient temperature, a solution of 24 g (0.6 mol) of sodium hydroxide in 100 ml of water is added; the resulting precipitate is separated off by filtration and washed copiously with water.

After drying, this gives the product of the formula

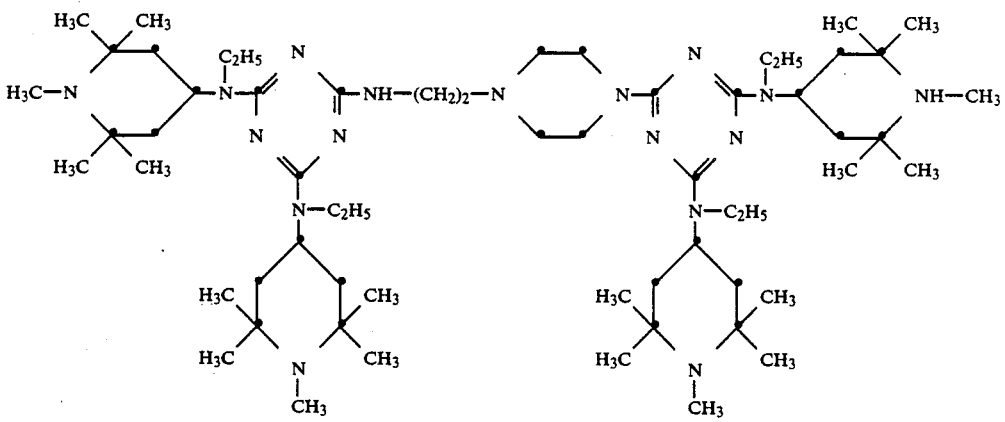

of melting point = 172°-177° C.
 Analysis for $C_{60}H_{113}N_{17}$:
 Calculated: C=67.18%, H=10.62 %, N=22.19%
 Found: C=66.97%, H=10.56%, N=22.00%

EXAMPLES 7-8:

Proceeding analogously to Example 6 and using the appropriate reagents, the following products of the formula are obtained.

| Example | R₃/R₅ | Melting point (°C.) |
|---|---|---|
| 7 | —C₄H₉-n | 132-135 |
| 8 | —CH₃ | 175-178 |

EXAMPLE 9:

52.61 g (0.036 mol) of the compound of Example 4, 400 ml of xylene, 13 g (0.43 mol) of paraformaldehyde and 5 g of 10% Pd on carbon are introduced into a 1 liter autoclave. After flushing with nitrogen, the compound is hydrogenated at 130°-140° C. under pressure of 40 bar.

When the absorption of hydrogen has ceased, the reaction mixture is cooled to ambient temperature, the catalyst is filtered off and the filtrate is evaporated in vacuo (26 mbar). After drying, this gives the product of the formula

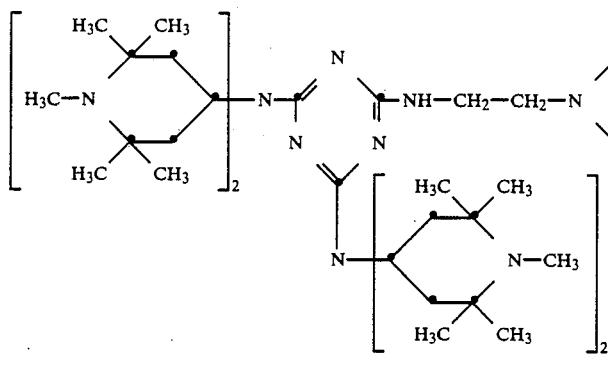
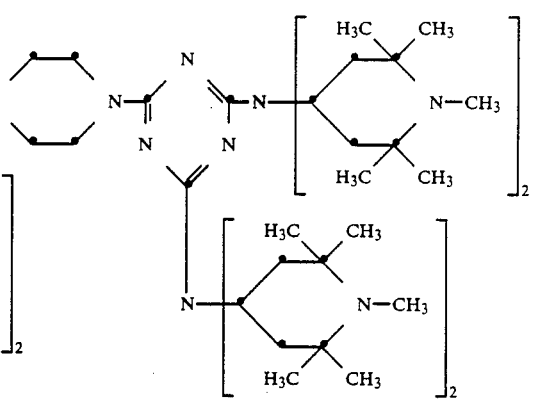

of melting point = 236–241° C.

Analysis for $C_{92}H_{173}N_{21}$:

Calculated: C = 70.23 %, H = 11.08 %, N = 18.69 %

Found: C = 69.41 %, H = 10.99 %, N = 18.61 %

EXAMPLE 10: Antioxidant action in polypropylene plaques 1 g of each of the compounds indicated in Table 1 and 1 g of calcium stearate are mixed in a slow mixer with 1,000 g of polypropylene powder of melt index = 2 g/10 minutes (measured at 230° C. and 2.16 kg).

The mixtures are extruded twice at 200–220° C. to give polymer granules which are then converted into plaques of 1 mm thickness (mould according to DIN 53,451) by means of compression-moulding for 3 minutes at 220° C.

The plaques obtained are exposed in a forced-circulation air oven, maintaining the temperature at 135° C. The specimens are checked periodically by folding them at 180° in order to determine the time (in hours) required to cause embrittlement.

The results obtained are shown in Table 1.

TABLE 1

| Stabilizer | Embrittlement time (hours) |
|---|---|
| Without stabilizer | 250 |
| Compound of Example 1 | 1360 |
| Compound of Example 2 | 1600 |
| Compound of Example 4 | 1560 |
| Compound of Example 6 | 1550 |
| Compound of Example 8 | 1350 |

EXAMPLE 11: Light stabilizing action in polypropylene tapes 1 g of each of the compounds indicated in Table 2, 0.5 g of tris(2,4-di-t-butylphenyl) phosphite, 0.5 g of pentaerythritol tetrakis[3-(3,5-di-t-butyl-4-hydroxyphenyl)-propionate] and 1 g of calcium stearate are mixed in a slow mixer with 1,000 g of polypropylene powder of melt index = 2 g/10 minutes (measured at 230° C. and 2.16 kg).

The mixtures are extruded at 200°–220° C. to give polymer granules which are then converted into stretched tapes of 50 pm thickness and 2.5 mm width, using a pilot type apparatus (Leonard-Sumirago (VA) Italy) under the following working conditions:

extruder temperature: 210°–230° C.

head temperature: 240°–260° C.

stretch ratio: 1:6

The tapes thus prepared are exposed, mounted on a white card, in a model 65 WR Weather-O-Meter (ASTM G 26-77), with a black panel temperature of 63° C.

The residual tenacity is measured on samples taken after various times of exposure to light, by means of a constant-speed tensometer; the exposure time in hours ($T_{50}$) needed to halve the initial tenacity is then calculated.

The results obtained are shown in Table 2.

TABLE 2

| Stabilizer | $T_{50}$ (hours) |
|---|---|
| Without stabilizer | 370 |
| Compound of Example 1 | 1530 |
| Compound of Example 2 | 1560 |
| Compound of Example 4 | 1610 |
| Compound of Example 6 | 1580 |
| Compound of Example 8 | 1490 |
| Compound of Example 9 | 1690 |

What is claimed is:

1. A composition comprising a polymer, resin or lubricating oil subject to thermal, oxidative or light-induced degradation and an effective heat, oxidation or light stabilizing amount of a compound of the formula I

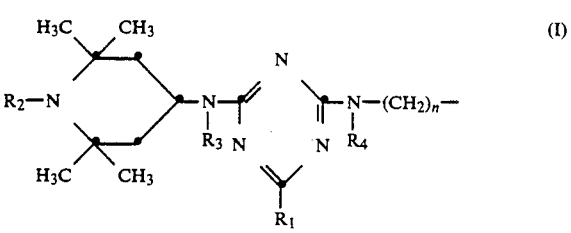

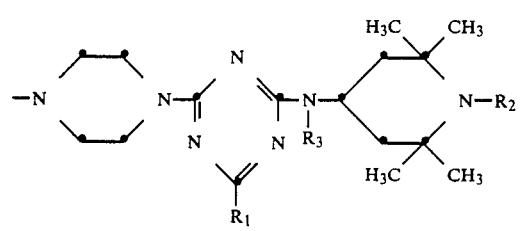

in which

R₁ is $C_1$–$C_8$-alkyloxy, allyloxy, allylamino, di($C_1$–$C_4$-alkyl)amino, diallylamino, 1-pyrrolidyl, 1-piperidyl, 4-morpholinyl, 1-hexahydroazepinyl, 4-methyl-1-piperazinyl, or a group of the formula (II),

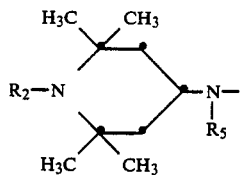  (II)

R₂ is hydrogen, O—, OH, NO, CH₂CN, $C_1$–$C_8$-alkyl, allyl, benzyl, $C_1$–$C_8$-acyl, $C_1$–$C_{18}$-alkyloxy, $C_5$–$C_{12}$-cycloalkyloxy or OH-monosubstituted $C_2$–$C_4$-alkyl, R₃ and R₅ independently are hydrogen, $C_1$–$C_{12}$-alkyl, $C_5$–$C_{12}$-cycloalkyl, $C_7$–$C_9$-phenylalkyl, tetrahydrofurfuryl, $C_2$–$C_4$-alkyl monosubstituted by OH, by $C_1$–$C_4$-alkyloxy or by di($C_1$–$C_4$-alkyl)amino, or a group of the formula (III)

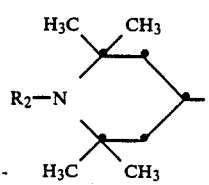  (III)

with R₂ as defined above, R₄ is hydrogen, $C_1$–$C_{12}$-alkyl or cyclohexyl and n is an integer from 2 to 6.

2. A method for stabilizing a polymer, resin or lubricating oil against thermal, oxidative or light-induced degradation, which comprises incorporating into the organic material an effective heat, oxidation or light stabilizing amount of a compound of the formula (I)

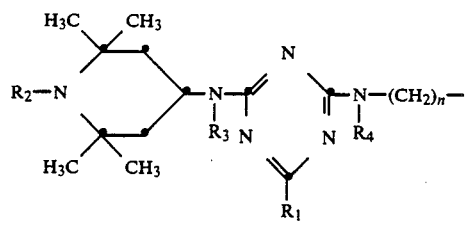  (I)

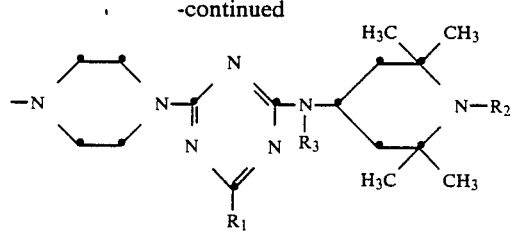

in which

R₁ is $C_1$–$C_8$-alkyloxy, allyloxy, allylamino, di($C_1$–$C_4$-alkyl)amino, diallylamino, 1 pyrrolidyl, 1-piperidyl, 4-morpholinyl, 1-hexahydroazepinyl, 4-methyl-1-piperazinyl, or a group of the formula (II),

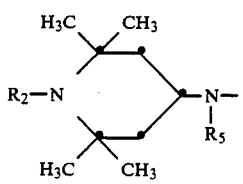  (II)

R₂ is hydrogen, O-, OH, NO, CH₂CN, $C_1$–$C_8$-alkyl, allyl, benzyl, $C_1$–$C_8$-acyl, $C_1$–$C_{18}$-alkyloxy, $C_5$–$C_{12}$-cycloalkyloxy or OH-monosubstituted $C_2$–$C_4$-alkyl, R₃ and R₅ independently are hydrogen, $C_1$–$C_{12}$-alkyl, $C_5$–$C_{12}$-cycloalkyl, $C_7$–$C_9$-phenylalkyl, tetrahydrofurfuryl, $C_2$–$C_4$-alkyl monosubstituted by OH, by $C_1$–$C_4$-alkyloxy or by di($C_1$–$C_4$-alkyl)amino, or a group of the formula (III)

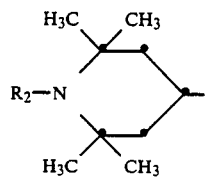  (III)

with R₂ as defined above, R₄ is hydrogen, $C_1$–$C_{12}$-alkyl or cyclohexyl and n is an integer from 2 to 6.

3. A composition according to claim 1, wherein the polymer is a synthetic polymer.

4. A composition according to claim 3, which, in addition to the compound of the formula (I), also comprises other conventional additives for synthetic polymers.

5. A composition according to claim 1, wherein the polymer is a polyolefine.

6. A composition according to claim 1, wherein the polymer is polyethylene or polypropylene.

* * * * *